US009549936B2

(12) United States Patent
Kim et al.

(10) Patent No.: US 9,549,936 B2
(45) Date of Patent: Jan. 24, 2017

(54) METHOD FOR PREPARING DRY POWDER FOR INHALATION FORMULATION COMPRISING SALMETEROL XINAFOATE, FLUTICASONE PROPIONATE AND TIOTROPIUM BROMIDE

(71) Applicant: HANMI PHARM. CO., LTD., Hwaseong-si, Gyeonggi-do (KR)

(72) Inventors: Kyeong Soo Kim, Suwon-si (KR); Deokkyu Lee, Seoul (KR); Dong Ho Kim, Seongnam-si (KR); Yong Il Kim, Suwon-si (KR); Jae Hyun Park, Suwon-si (KR); Jong Soo Woo, Suwon-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 14/746,225

(22) Filed: Jun. 22, 2015

(65) Prior Publication Data

US 2015/0283151 A1 Oct. 8, 2015

Related U.S. Application Data

(62) Division of application No. 14/402,548, filed as application No. PCT/KR2013/004880 on Jun. 3, 2013, now Pat. No. 9,283,232.

(30) Foreign Application Priority Data

Jun. 14, 2012 (KR) ........................ 10-2012-0063665

(51) Int. Cl.

| A61K 9/50 | (2006.01) |
|---|---|
| A61K 31/56 | (2006.01) |
| A61K 9/00 | (2006.01) |
| A61K 9/14 | (2006.01) |
| A61K 31/137 | (2006.01) |
| A61K 31/439 | (2006.01) |
| A61K 31/136 | (2006.01) |
| A61K 31/46 | (2006.01) |
| A61K 31/568 | (2006.01) |
| A61K 47/26 | (2006.01) |

(52) U.S. Cl.

CPC ............ *A61K 31/56* (2013.01); *A61K 9/0075* (2013.01); *A61K 9/145* (2013.01); *A61K 31/136* (2013.01); *A61K 31/137* (2013.01); *A61K 31/439* (2013.01); *A61K 31/46* (2013.01); *A61K 31/568* (2013.01); *A61K 47/26* (2013.01)

(58) Field of Classification Search

None
See application file for complete search history.

(56) References Cited

U.S. PATENT DOCUMENTS

| 2003/0152523 A1* | 8/2003 | Martin ................. A61K 9/0075 424/46 |
|---|---|---|
| 2005/0042174 A1 | 2/2005 | Nilsson et al. |
| 2009/0088408 A1 | 4/2009 | Meade et al. |
| 2010/0063016 A1 | 3/2010 | Lulla et al. |
| 2010/0329996 A1* | 12/2010 | Laine .................. A61K 31/138 424/45 |

FOREIGN PATENT DOCUMENTS

| KR | 10-2009-0121338 A | 11/2009 |
|---|---|---|
| WO | 95/11666 A1 | 5/1995 |
| WO | 2004105727 A2 | 12/2004 |
| WO | 2005046636 A1 | 5/2005 |
| WO | 2010/007446 A1 | 1/2010 |
| WO | 2011105975 A1 | 9/2011 |

OTHER PUBLICATIONS

European Patent Office, Communication dated Sep. 28, 2015 issued in counterpart EP application No. 13804439.1.
International Searching Authority, International Search Report for PCT/KR2013/004880 dated Sep. 13, 2013.
Shawn D. Aaron et al., "Tiotropium in Combination with Placebo, Salmeterol, or Fluticasone-Salmeterol for Treatment of Chronic Obstructive Pulmonary Disease", Annals of Internal Medicine, 2007, pp. 545-555, vol. 146.
D. Singh et al., "Superiority of "triple" therapy with salmeterol/fluticasone propionate and tiotropium bromide versus, individual components in moderate to severe COPD", Thorax, 2008, pp. 592-598, vol. 63.
Mario Cazzola et al., "A pilot study to assess the effects of combining fluticasone propionate/salmeterol and tiotropium on the airflow obstruction of patients with severe-to-very severe COPD", Pulmonary Pharmacology & Therapeutics, 2007, pp. 556-561, vol. 20.
International Searching Authority, Written Opinion for PCT/KR2013/004880 dated Sep. 13, 2013.
Intellectual Property Office of Singapore, Communication dated Dec. 18, 2015, issued in corresponding Singapore Application No. 11201408292Y.
Intellectual Property Office of Singapore, Communication dated Feb. 18, 2016, issued in corresponding Singapore Application No. 11201408292Y.

(Continued)

*Primary Examiner* — Robert A Wax
*Assistant Examiner* — Quanglong Truong
(74) *Attorney, Agent, or Firm* — Sughrue Mion, PLLC

(57) ABSTRACT

Disclosed are a dry powder for inhalation formulation comprising salmeterol xinafoate, fluticasone propionate and tiotropium bromide, as pharmaceutically active ingredients, and a carrier, and an inhalation formulation comprising same and a method for preparing the same. The inventive dry powder inhalation formulation having good content uniformity and showing small changes in the aerodynamic size distribution in accordance with the flow rate changes can effectively deliver said pharmaceutically active ingredients to a target site upon administration, and thus can be useful in the prevention or treatment of respiratory diseases, particularly asthma and COPD.

5 Claims, 3 Drawing Sheets

(56) References Cited

OTHER PUBLICATIONS

Communication dated May 23, 2016 from New Zealand Intellectual Property Office in counterpart Application No. 703788.
Taiwan Intellectual Property Bureau Ministry of Economic Affairs, Communication dated May 25, 2015 issued in corresponding Taiwanese application No. 102120909.
Chrystyn, H., Int. J. Clin. Pract., Jun. 2007, 61, 6, 1022-1036.
Xu et al., J. Int. Pharm. Res., Feb. 2011, vol. 38, No. 1, 42-48.

* cited by examiner

Aerodynamic size distribution of fluticasone

FIG. 3

Aerodynamic size distribution of tiotropium

METHOD FOR PREPARING DRY POWDER FOR INHALATION FORMULATION COMPRISING SALMETEROL XINAFOATE, FLUTICASONE PROPIONATE AND TIOTROPIUM BROMIDE

The present application is a divisional of U.S. application Ser. No. 14/402,548 filed Nov. 20, 2014, which is a National Stage of International Application No. PCT/KR2013/004880, filed on Jun. 3, 2013, which claims the benefit of priority from Korean Patent Application No. KR 10-2012-0063665, filed on Jun. 14, 2012, the contents of which are herein incorporated by reference in their entirety.

FIELD OF THE INVENTION

The present invention relates to a dry powder for inhalation formulation comprising salmeterol xinafoate, fluticasone propionate and tiotropium bromide, and method for preparing same.

BACKGROUND OF THE INVENTION

Various medicaments have been used in the form of inhalation formulation for the treatment of respiratory diseases, e.g., asthma and chronic obstructive pulmonary disease (COPD). A particular advantage of inhalation formulation is that only a small amount of a pharmaceutically active ingredient is required to achieve the desired therapeutic effect; however, there are drawbacks to the formulation that only a part of the pharmaceutically active ingredient administered will be delivered to a target site, or there is a great possibility that the pharmaceutically active ingredient will be delivered to sites where no treatment is required, thereby causing adverse side effects. Thus, continuous efforts are being made to maximize the therapeutic effect of the formulation so as to achieve reliable targeted delivery to the site where the therapeutic effect is desired and to prevent the delivery of the pharmaceutically active ingredient to the site where no treatment is required.

For effective administration of inhalation formulation, inhalers, which administer the drug by sucking in the air with the drug and delivering them into the air passage, have been widely used for treatment of respiratory diseases. The most common inhaler systems are metered dose inhalers (MDI), which had been used extensively since its approval in 1956, and once occupied 80% of the inhaler market. However, a rise of environmental concerns, e.g., depletion of ozone layer and global warming, has shifted research interests to focus on dry powder inhalers (DPI) in recent years. In current stage, researchers are concentrating their efforts to remedy the shortcomings of MDI formulations by employing DPI formulations. MDIs typically comprise pharmaceutically active ingredients and a solvent as a propellant in compressed state, which deteriorates its stability; and the spraying speed is fast, and thus it reaches laryngopharyngeal space too fast. DPIs, however, are easy to use; and only comprised of powder solid particles, and therefore are advantageous in terms of stability (see Martin J Telko and Anthony J Hickey, Dry Powder Inhaler Formulation, Respiratory Care, September 2005, Vol 50, No. 9).

Meanwhile, various drugs are being tested for the prevention and treatment of respiratory diseases. For example, a selective beta-2 adrenoceptor agonist (beta-2 agonist) can induce bronchodilation, and can be used to relieve respiratory distress. Beta-2 agonists may be broadly divided into short-acting beta-2 agonists and long-acting beta-2 agonists. Short-acting beta-2 agonists, e.g., salbutamol, fenoterol, levalbuterol, terbutaline, etc., provide immediate relief, but their reaction time is rather short. In contrary, long-acting beta-2 agonists, e.g., formoterol, indacaterol, salmeterol, tulobuterol, etc., provide sustained bronchodilation, but patients are required to take them two or more times per day because the normal reaction time of these drugs is less than 12 hours.

Beta-2 agonists can alleviate bronchoconstriction in patients, but other drugs, e.g., steroids, are used to treat inflammation, which is another cause of asthma. Examples of steroids include inhaled corticosteroid (ICS) such as beclomethasone, budesonide, flunisolide, fluticasone propionate, mometasone furoate, triamcinolone, and the like.

Also, another type of drugs called an inhaled anticholinergic is well-known as a stable and effective bronchodilator which can be used for treatment of COPD. Anticholinergic agents can increase the level of forced expiratory volume in 1 second (FEV1), prevent static or dynamic hyperinflation (overexpanded lung), and reduces exacerbations of COPD. There is a limited number of inhaled anticholinergic bronchodilators that are currently available, e.g., rapid-onset types such as ipratropium bromide, oxitropium bromide, etc., and long-acting types such as tiotropium bromide, etc.

Global Initiative for Asthma (GINA) and Global Initiative for Chronic Obstructive Lung Disease (GOLD) are suggesting an incremental treatment method based on the progression of the disease condition, which includes the use of a combination formulation of drugs having different or complementary action mechanisms. For instance, a long-acting beta-2 agonist is prescribed to patients with asthma or COPD having FEV1 level of less than 80%, and COPD patients with accompanying respiratory distress having FEV1 level of less than 50% or who are experiencing frequent acute exacerbations are prescribed with ICS in addition to beta-2 agonists.

A number of combinations of the aforementioned drugs are known already, and one typical example is an inhalation formulation comprising salmeterol xinafoate and fluticasone propionate (Seretide, GSK). Currently, Seretide is available in MDI (Evohaler) and DPI (Diskus) formulations. Seretide provides an effective bronchodilation induced by the long-acting beta-2 agonist salmeterol, as well as potent anti-inflammatory action caused by the ICS, fluticasone propionate. In case of Seretide Diskus formulation, which is provided in the form of DPI formulation, both beta-2 agonist and inhaled corticosteroid may be inhaled at once, but the formulation does not show sustained bronchodilation action, and thus patients are required to take the formulation two or more times per day. Another drawback of this formulation lies in that the amount of the excipient is too small to give a sensation in the lungs upon administration, and sometimes the dose is not properly delivered or is taken two or more times because it is impossible to observe administered formulation.

Also, a combination therapy comprising a rapid-onset anticholinergics ipratropium bromide and a long-acting beta-2 agonist salmeterol is disclosed in WO01/76601, and an additional combination therapy using anticholinergics, beta-2 agonist as well as steroid is disclosed in U.S. Pat. No. 6,423,298 and WO02/7672.

Nevertheless, said formulations do not relate to a triple combination formulation which can exert fast-acting bronchodilation induced by a beta-2 agonist, anti-inflammatory action by a corticosteroid, and sustained bronchodilation by an anticholinergic at once.

Recently, KR Patent Laid-Open Publication No 10-2009-0121338 and US Patent Application Publication No. 2010/0063016 mentioned about a triple combination formulation of beta-2 agonist, corticosteroid, and anticholinergic. However, they neither consider any specific device, effective dose amount, manufacturing method thereof, packaging type, particle size of the carrier material, etc., nor provide assessment data thereof. Pressure drop values of inhalation formulations, especially in the form of dry powder inhalation formulations, vary when different types of devices are used, and the amount of active ingredient delivered to lungs may vary with packaging forms, e.g., blister packaging vs. capsule packaging. Properties and ratio of excipient (such as lactose, etc.), which is used as a carrier, can also cause a large difference in therapeutic effects. Moreover, even if drugs from the same drug group were used, undesirable results such as deterioration in uniformity and storage stability may occur depending on physicochemical properties of the respective drugs.

Although some drugs and a combination formulation thereof for the prevention or treatment of respiratory diseases are known, there are no specific compositions or preparation method thereof developed for a triple combination formulation which can administer a long-acting beta-2 agonist, an inhaled corticosteroid and an anticholinergic together at once. Thus, there has been a need to develop a composition of a composite formulation, which can stably and accurately administer said three groups of drug in a single dose, to improve patient compliance and enhance patients' convenience to carry the formulation.

SUMMARY OF THE INVENTION

Therefore, it is an object of the present invention to provide a dry powder for inhalation formulation comprising salmeterol xinafoate, fluticasone propionate and tiotropium bromide, having good content uniformity and showing small changes in the aerodynamic size distribution in accordance with the flow rate changes, which can effectively deliver said pharmaceutically active ingredients to a target site upon administration.

It is another object of the present invention to provide an inhalation formulation comprising the dry powder.

It is still another object of the present invention to provide a method for preparing the dry powder for inhalation formulation.

In accordance with one object of the present invention, there is provided a dry powder for inhalation formulation comprising salmeterol xinafoate, fluticasone propionate, tiotropium bromide, and a carrier, having an average particle size in a range of 30 to 120 μm.

In accordance with another object of the present invention, there is provided an inhalation formulation comprising the dry powder for inhalation formulation.

In accordance with still another object of the present invention, there is provided a method for preparing the dry powder for inhalation formulation, which comprises the steps of: (1) applying 5 to 20 wt % of a carrier, based on the total amount of the carrier, onto inner walls of a mixer; (2) triturating salmeterol xinafoate, fluticasone propionate and tiotropium bromide with 5 to 20 wt % of the carrier, based on the total amount of the carrier; and (3) placing the triturated ingredients and the remaining carrier in the mixer prepared in Step (1), and then pulverizing the mixture with a force not sufficient to substantially alter the size of the particles, followed by admixing.

The dry powder for inhalation formulation according to the present invention having good content uniformity and small changes in the aerodynamic size distribution in accordance with the flow rate changes can deliver said three active ingredients together upon administration, thereby enhancing patients' convenience to carry the formulation as well as improving patient compliance, and thus have good therapeutic compliance in the treatment of respiratory diseases, particularly in asthma and COPD.

BRIEF DESCRIPTION OF DRAWINGS

FIG. 1 shows the analysis of the aerodynamic size distribution of salmeterol in accordance with Test Example 2.

FIG. 2 shows the analysis of the aerodynamic size distribution of fluticasone in accordance with Test Example 2.

FIG. 3 shows the analysis of aerodynamic size distribution of tiotropium in accordance with Test Example 2.

DETAILED DESCRIPTION OF THE INVENTION

The dry powder for inhalation formulation in accordance with the present invention comprises, as active ingredients, salmeterol xinafoate as a long-acting beta-2 agonist, fluticasone propionate as an inhaled corticosteroid, and tiotropium bromide as an anticholinergic agent, and additionally a carrier, having an average particle size in a range of 30 to 120 μm.

In the present invention, specific salts or solvates of each active ingredient were employed; however, those skilled in the art may employ any equivalents having the same or similar activities in lieu of the specific salts or solvates. Examples of the equivalents include pharmaceutically acceptable salts, solvates, hydrates, enantiomers, derivatives, polymorphs, and prodrugs thereof, but not limited thereto.

In order to effectively deliver the pharmaceutically active ingredients to a lung to exert pharmacological activity, particles of each active ingredient must be micronized. Generally, the size of a particle which is suitable to be administered by inhalation is greater than 0.1 μm and less than or equal to 10 μm, preferably greater than 0.1 μm and less than or equal to 5 μm. If the size of the particle is 0.1 μm or smaller, the particles may be discharged from the body, rather than being absorbed by the bronchial tube. Hence, according to USP 34 <601>'Aerosol, Nasal spray, Metered-dose inhaler and Dry powder inhaler,' various equipments, e.g., Apparatus 1~6, are suggested to measure the aerodynamic size distribution for MDI and DPI formulations. For example, one can determine that the main ingredient collected during stages 1~5 has the aerodynamic size distribution in a range of 0.1 to 5 μm when using Apparatus 3 (Anderson Cascade Impactor) of USP 34 <601>, which allows prediction of the effective amount which can exert pharmacological activity upon administration of inhalation formulation by measuring the amount. Generally, the particle size distribution which covers this area is preferably 10 to 30% of the active ingredient content measured for inhalation.

However, small particles are thermodynamically unstable due to their high surface area to volume ratio, and an excessive surface free energy may cause particles to agglomerate easily. When the particles agglomerate, they are attached to the capsule or the inner wall of the inhalation device to interrupt the release of the powder. Therefore, pharmaceutically acceptable excipients, i.e., carrier particles, may be employed so as to redress such problems.

Specifically, it is preferred that micronized pharmaceutically active ingredients are attached to carrier particles to yield thermodynamic stability, prevent agglomeration, and thus effectively transport the particles inside the body upon inhalation. Also, the pharmaceutically active ingredients should be easily discharged from the surface of the carrier particles in the respiratory tract to reach target sites once administered. Generally, the size of carrier particles is considerably large so that they cannot reach target sites directly, and thus, if the active ingredients are not easily discharged from the carrier, the amount of the pharmaceutically active ingredients that can reach target sites would significantly decrease. Meanwhile, the flowability of the carrier particle increases with the size of the particle, therefore the size of the carrier should be large enough to transport the particle out of the inhalation device easily.

Accordingly, the size of the carrier used in the dry powder for an inhalation formulation must be suitable to yield good flowability. In one embodiment, the size of the carrier particle is 30 to 120 μm. Such carrier particle may be mixed with micronized carriers to allow uniform attachment of the pharmaceutically active ingredient particles to the carrier particles and also make it easy to discharge the pharmaceutically active ingredient particles from the carrier particles in the respiratory tract. In general, this can be accomplished by attaching a small amount of micronized carrier particles primarily to the irregular surface of the carrier particles, so that the micronized carrier particles are attached to the surface with a high surface energy first to lower the surface energy thereof, lowering overall surface energy and allowing the carrier particles to have homogeneous distribution of surface energy. The average diameter of the micronized carrier particles may be 35 μm or less, preferably 30 μm or less, more preferably 25 μm or less. Further, the micronized carrier particles may be used in such an amount that the flowability of the inhalation composition will not be affected, e.g., 0.1 to 20 wt % based on the total weight of carrier particles. In an embodiment, the micronized carrier particle may be used in an amount of 1 to 15 wt %, and in another embodiment, the micronized carrier particle may be used in an amount of 3 to 12 wt %. Generally, micronized carrier particles may be mixed with carrier particles; alternatively, commercially available carrier particles with uniform size may be employed in the present invention.

Also, the surface properties of the carrier particles are important factors which affect the discharge of the pharmaceutically active ingredients from the inhalation device or the delivery of the active ingredients to the target sites. The pharmaceutically active ingredients are required to have enough adhesion force with the surface of the carrier particles to allow good flowability so that they can be easily discharged from the inhalation device; at the same time, the pharmaceutically active ingredients must be easily discharged from the surface of the carrier in the respiratory tract so as to reach the target sites once it leaves the inhalation device, and thus there is a difficulty in maintaining an appropriate adhesion force between the surface of the carrier and the pharmaceutically active ingredients. In the present invention, the pharmaceutically active ingredients and the carriers are subjected to a soft pulverization and a mixing process, to yield a suitable adhesion force between them.

Selecting an excipient as a carrier is an important factor in the composition of an inhalation formulation, particularly a composite inhalation formulation comprising two or more of pharmaceutically active ingredients. Examples of the excipient employable for the present invention include monosaccharides such as glucose, arabinose; disaccharides such as lactose, maltose, sucrose; polysaccharides such as starch, dextrin or dextran; polyalcohols such as sorbitol, mannitol, and xylitol; and hydrates thereof. In an embodiment of the present invention, monosaccharides or disaccharides are employed as an excipient; in another embodiment of the present invention, lactose is employed; and in still another embodiment of the present invention, lactose monohydrate is used.

Selecting an appropriate amount of the carrier is also important. An excessive amount of the carrier in the formulation not only causes patients to feel unpleasant due to excessive foreign body sensation, but also could cause asthma due to the carrier, a foreign body. Moreover, if the amount employed is too small, it becomes difficult to obtain uniformity between the carrier and the pharmaceutically active ingredients, and to measure one dose in a capsule or a blister packaging. Thus, in the present invention, the amount of the carrier employed is in a range of 15 mg to 25 mg. Said amount can be charged in a capsule or a blister packaging by conventional methods which do not requires any special equipment, giving the advantage that the formulation can be manufactured in conventional pharmaceutical manufacturing facilities without any modification.

In the inhalation formulations, however, the amount of the pharmaceutically active ingredient is very small as compared to the amount of the carrier. Since a conventional simple mixing may cause a difficulty in procuring the content uniformity, other methods such as trituration may be used to mix the active ingredient with the carrier so as to resolve such problem. Trituration refers to a method in which pharmaceutically active ingredients and excipients are mixed in a ratio of 1:1 to 1:4, e.g., 1:1, 1:2, or 1:4, and the excipients are added in the same ratio to the mixture prepared repeatedly until all the excipients are used up. Nevertheless, in the case of the inhalation formulations comprising pharmaceutically active ingredients with very small particle size which also take up relatively a very small portion of the total contents, there may be a problem with the content uniformity even by the trituration process.

Accordingly, a layered mixing process using a screening device was employed to maintain content uniformity as disclosed in KR Pat. No. 0849837. In this process, big and small particles, however, must be separated before using the process, and each of ten or more, preferably 30 or more, fractions are required to pass through the screening device, thereby causing a great inconvenience.

Therefore, the present inventors have endeavored to redress said problems and have discovered that subjecting the pharmaceutically active ingredients and the carriers to a soft pulverization and a mixing process could resolve the problem in the content uniformity of the inventive inhalation formulation. The term 'soft pulverization and mixing' as used herein, refers to the process of placing a powder in a blender equipped with a ball or chopper followed by mixing, wherein the pulverization is conducted by rotating the blender and the particles of the powder are pulverized by the ball or chopper with a force not sufficient to substantially alter the size of the particles, e.g., to a degree of less than 20% of the size change. The size of the carrier particles gets smaller when they are exposed to a strong physical force for a long period of time. If the size of the carrier particles is too small, then flowability of the powder deteriorates and the powder may remain in the inhalation device or the capsule, thereby causing a difficulty in delivering desirable amount of the pharmaceutically active ingredient to the target sites. In a preferred embodiment, the dry powder for inhalation formulation of the present invention has an average particle size in a range of 30 to 120 µm. If the average particle size is in the said range, the content uniformity of the pharmaceutically active ingredient is satisfactory and the particle size distribution does not fluctuate with the change in flow rate. However, if the average particle size exceeds 120 μm, the content uniformity deteriorates and causes the pharmaceutically active ingredients to remain in the inhalation device or the capsule when the formulation is inhaled. Also, if the average particle size is less than 30 μm, the effective amount of the pharmaceutically active ingredients is heavily changed depending on flow rate. In another preferred embodiment, the dry powder for inhalation formulation of the present invention has an average particle size in a range of 55 to 65 μm.

In the mixing process, a small amount of carrier is applied on the chopper and the walls of the blender, and then a certain amount of the carrier and the pharmaceutically active ingredients are triturated and sieved, followed by soft pulverization and mixing. Preferably, the amount of the carrier to be applied on the chopper and the walls is in a range of 5 to 20 wt %, based on the total amount of the carrier; and the amount of the carrier to be triturated with the pharmaceutically active ingredient is in a range of 5 to 20 wt %, based on the total amount of the carrier, but not limited thereto. The pharmaceutically active ingredients have very small sized particles and a high surface energy which gives them a sticky property, so there is a high possibility of loss in active ingredients if they were placed first in the blender because they could stick to the chopper and the walls of blender. Thus, this can be prevented by applying a suitable amount of the carrier having a good flowability onto the chopper and the walls of the blender. Next, the pharmaceutically active ingredients and the carrier are triturated and sieved, followed by a soft pulverization and a mixing process. Preferably, the mixing process is carried out at a relative humidity of 40 to 60%. If the relative humidity is too low, it becomes difficult to carry out the mixing process due to static electricity; and even if the mixing process is carried out successfully, there is a high chance of losing a large amount of the particles during the process. Also, if the relative humidity is too high, the particles have a tendency to absorb moisture and to form agglomerates. Due to its hygroscopic properties, the stability of salmeterol xinafoate, in particular, cannot be secured if it is exposed to an excessive amount of moisture during a long-term storage.

As explained above, the present invention provides a method for preparing the dry powder for inhalation formulation, which comprises the steps of: (1) applying 5 to 20 wt % of the carrier, based on the total amount of the carrier, on inner walls of a mixer; (2) triturating salmeterol xinafoate, fluticasone propionate and tiotropium bromide with 5 to 20 wt % of the carrier, based on the total amount of the carrier; and (3) placing the triturated ingredients and the remaining carrier in the mixer prepared in Step (1), and then pulverizing the mixture with a force not sufficient to substantially alter the size of the particles, followed by admixing.

Meanwhile, the present invention provides an inhalation formulation comprising the dry powder contained in the form of a capsule and a cartridge comprising gelatin or hypromellose, or a blister pack comprising a plurality of aluminum thin layers, preferably in the form of a capsule. The capsule size of the inventive formulation is preferably No. 1 to No. 4. In one embodiment of the present invention, the capsule size is No. 3. One of the advantages of preparing the formulation in the form of the capsule is that it can be manufactured without requiring any special equipment. Also, the capsule, which is charged with the composition of the present invention, is preferably made of a transparent material. If the inventive formulation is provided in a transparent capsule, patients can check whether or not they have taken the required medication properly after they were administered with the inventive formulation with their own eyes. Also, the patients can check for product defects or deterioration of the quality in the dry powder such as agglomeration or discoloration with their eyes before they take the formulation.

The device used for administration of the dry powder refers to a device which breaks, punches or uses any other method to open the capsule to allow delivery of the weighed compositions to the lung of a patient. Also, the device may further comprise an air inlet which creates an air flow where air enters the device, an air outlet which discharges the pharmaceutically active ingredients when patients inhale the air, and a particulate filter to filter any impurities. Examples of such devices that are currently available in the market include ROTAHALER® (GSK), HANDIHALER® (Boehringer Ingelheim), and AEROLIZER® (PLASTIAPE). The inhalation formulation in accordance with the present invention may be used with any device which can utilize a capsule composition, preferably AEROLIZER®. In the device, there is a hole in the center of the device to place a capsule and when the buttons on the sides are pressed, pins come out to punch holes to make ready for the administration of the formulation. The device is relatively small, and hence has good portability.

In the DPI inhalation device as described above, the driving force which takes in the pharmaceutically active ingredients from the capsule is the inhalation force of the patient. All DPI devices have the pressure drop value which is induced by airflow when the patient is administered with the formulation, and the pressure drop values which vary with the airflow can be the important variable in aerodynamic size distribution and content uniformity tests for evaluation of the effective amount suitable for the inhalation formulation. In fact, peak inspiratory flow value will differ, e.g., from 10 to 100 L/min, depending on the type of device used, age of the patient and condition of the disease. The United State Pharmacopoeia suggests that a flow rate can be controlled from 0 to 100 L/min, and a flow rate that creates a pressure drop of 4 kPa across the inhaler ($Q_{out}$) and a suction time (T) obtained from the formula $T(sec)=240/Q_{out}$ may be used to evaluate the tests results. Thus, it is preferable that the inventive formulation has small changes in the aerodynamic size distribution in accordance with the flow rate changes so as to give similar pharmaceutical effects among patients. The dry powder inhalation formulation in accordance with the present invention has an advantage that the aerodynamic size distribution of three pharmaceutically active ingredients does not fluctuate depending on the flow rate changes.

Therefore, the dry powder inhalation formulation in accordance with the present invention can effectively release the mixture from the inhalation device; easily discharge the pharmaceutically active ingredient from carrier in respiratory tract, thereby delivering the active ingredients to the target sites effectively; and show good content uniformity of pulverized pharmaceutically active ingredient and small changes in the aerodynamic size distribution in accordance with the flow rate changes.

In the dry powder inhalation formulation in accordance with the present invention, salmeterol xinafoate, fluticasone propionate and tiotropium bromide may be employed in amounts of 25 to 100 μg, 25 to 500 μg, and 5 to 50 μg, respectively, per dosage unit. However, employable amounts are not limited thereto, and may be adjusted depending on the various factors, e.g., the patient and disease condition being treated.

The dry powder inhalation formulation of the present invention comprising salmeterol, fluticasone and tiotropium can effectively control bronchoconstriction, inflammation and secretion of the mucus in the respiratory tract, and thus can be useful in the treatment of respiratory diseases, particularly asthma and COPD.

Hereinafter, the present invention is described more specifically by the following examples, but these are provided only for illustration purposes, and the present invention is not limited thereto.

EXAMPLE 1

Preparation of Dry Powder Inhalation Formulation I 2 mg of lactose is placed in a mixer to be applied onto the mixer. Salmeterol xinafoate, fluticasone propionate and tiotropium bromide in accordance with the compositions listed in Table 1, and 2 mg of lactose were triturated and placed in the mixer, and then the remaining lactose was placed in the mixer with balls, followed by admixing for 20 minutes. The mixture obtained was stabilized for 12 hours or more, and charged in a transparent size No. 3 capsule by using a capsule filling machine. The deviation of the contents charged in the capsules was satisfactory, which came out to be 3.4%, and the average particle size of the said composition was 60.19 μm as measured with a Sympatec HELOS laser diffraction sensor.

TABLE 1

| Ingredient | (mg) |
| --- | --- |
| Salmeterol xinafoate | 0.0725 (salmeterol 0.05) |
| Fluticasone propionate | 0.2500 |
| Tiotropium bromide | 0.0225 (tiotropium 0.018) |
| Lactose | 20.0000 |
| Total | 20.3450 |

EXAMPLE 2

Preparation of Dry Powder Inhalation Formulation II

The procedures of Example I were repeated, except for using tiotropium bromide in an amount of 0.01125 mg in accordance with Table 2 below, to obtain the dry powder inhalation formulation. The deviation of the contents charged in the capsules was satisfactory, which came out to be 3.1%, and the average particle size of the said composition was 58.34 μm.

TABLE 2

| Ingredient | (mg) |
| --- | --- |
| Salmeterol xinafoate | 0.0725 (salmeterol 0.05) |
| Fluticasone propionate | 0.2500 |
| Tiotropium bromide | 0.01125 (tiotropium 0.009) |
| Lactose | 20.0000 |
| Total | 20.33375 |

EXAMPLE 3

Preparation of Dry Powder Inhalation Formulation III

The procedures of Example I were repeated, except for using fluticasone propionate in an amount of 0.5000 mg in accordance with Table 3 below, to obtain the dry powder inhalation formulation. The deviation of the contents charged in the capsules was satisfactory, which came out to be 4.5%, and the average particle size of the said composition was 56.91 μm.

TABLE 3

| Ingredient | (mg) |
| --- | --- |
| Salmeterol xinafoate | 0.0725 (salmeterol 0.05) |
| Fluticasone propionate | 0.5000 |
| Tiotropium bromide | 0.0225 (tiotropium 0.018) |
| Lactose | 20.0000 |
| Total | 20.5950 |

EXAMPLE 4

Preparation of Dry Powder Inhalation Formulation IV

The procedures of Example I were repeated, except for using fluticasone propionate in an amount of 0.1000 mg and tiotropium bromide in an amount of 0.01125 mg in accordance with Table 4 below, to obtain the dry powder inhalation formulation. The deviation of the contents charged in the capsules was satisfactory, which came out to be 3.9%, and the average particle size of the said composition was 62.48 μm.

TABLE 4

| Ingredient | (mg) |
| --- | --- |
| Salmeterol xinafoate | 0.0725 (salmeterol 0.05) |
| Fluticasone propionate | 0.1000 |
| Tiotropium bromide | 0.01125 (tiotropium 0.009) |
| Lactose | 20.0000 |
| Total | 20.18375 |

EXAMPLE 5

Preparation of Dry Powder Inhalation Formulation V

The procedures of Example I were repeated, except for using lactose in an amount of 15 mg in accordance with Table 5 below, to obtain the dry powder inhalation formulation. The deviation of the contents charged in the capsules was satisfactory, which came out to be 4.8%, and the average particle size of the said composition was 63.57 μm.

TABLE 5

| Ingredient | (mg) |
| --- | --- |
| Salmeterol xinafoate | 0.0725 (salmeterol 0.05) |
| Fluticasone propionate | 0.2500 |

TABLE 5-continued

| Ingredient | (mg) |
| --- | --- |
| Tiotropium bromide | 0.0225 (tiotropium 0.018) |
| Lactose | 15.0000 |
| Total | 15.3450 |

EXAMPLE 6

Preparation of Dry Powder Inhalation Formulation VI

The procedures of Example I were repeated, except for using lactose in an amount of 25 mg in accordance with Table 6 below, to obtain the dry powder inhalation formulation. The deviation of the contents charged in the capsules was satisfactory, which came out to be 3.2%, and the average particle size of the said composition was 58.72 μm.

TABLE 6

| Ingredient | (mg) |
| --- | --- |
| Salmeterol xinafoate | 0.0725 (salmeterol 0.05) |
| Fluticasone propionate | 0.2500 |
| Tiotropium bromide | 0.0225 (tiotropium 0.018) |
| Lactose | 25.0000 |
| Total | 25.3450 |

COMPARATIVE EXAMPLE 1

Preparation of Dry Powder Inhalation Formulation VII

In accordance with Table 7 below, salmeterol xinafoate, fluticasone propionate, tiotropium bromide and lactose were placed in a mixer together, followed by admixing for 60 minutes. The mixture obtained was stabilized for 12 hours or more, and charged in a transparent size No. 3 capsule by using a capsule filling machine. The deviation of the contents charged in the capsules was satisfactory, which came out to be 4.9%, and the average particle size of said composition was 145.39 μm.

TABLE 7

| Ingredient | (mg) |
| --- | --- |
| Salmeterol xinafoate | 0.0725 (salmeterol 0.05) |
| Fluticasone propionate | 0.2500 |
| Tiotropium bromide | 0.0225 (tiotropium 0.018) |
| Lactose | 20.0000 |
| Total | 20.3450 |

COMPARATIVE EXAMPLE 2

Preparation of Dry Powder Inhalation Formulation VIII

The procedures of Comparative Example I were repeated, except for using lactose in an amount of 5 mg in accordance with Table 8 below, to obtain the dry powder inhalation formulation. The average particle size of the said composition was 140.56 μm.

TABLE 8

| Ingredient | (mg) |
| --- | --- |
| Salmeterol xinafoate | 0.0725 (salmeterol 0.05) |
| Fluticasone propionate | 0.2500 |
| Tiotropium bromide | 0.0225 (tiotropium 0.018) |
| Lactose | 5.0000 |
| Total | 5.3450 |

COMPARATIVE EXAMPLE 3

Preparation of Dry Powder Inhalation Formulation IX

In accordance with the compositions listed in Table 9, the procedures of Example 1 was repeated using lactose, i.e., Respitose® ML006 (DMV) having an average particle size of approximately 17 μm to prepare a mixture. The mixture obtained was stabilized for 12 hours or more, and charged in a transparent size No. 3 capsule by using a capsule filling machine. The deviation of the contents charged in the capsules was unsatisfactory, which came out to be 7.4%, and the average particle size of the said composition, measured by laser diffraction sensor HELOS (Sympatec) was 14.63 μm.

TABLE 9

| Ingredient | (mg) |
| --- | --- |
| Salmeterol xinafoate | 0.0725 (salmeterol 0.05) |
| Fluticasone propionate | 0.2500 |
| Tiotropium bromide | 0.0225 (tiotropium 0.018) |
| Lactose | 20.0000 |
| Total | 20.3450 |

TEST EXAMPLE 1

Evaluation of Content Uniformity

Capsule formulations obtained in Examples 1 and 2 and Comparative Example 1 were subjected to content uniformity evaluation of salmeterol, fluticasone and tiotropium under the following conditions. The results are shown in Tables 10 to 12. The acceptance value according to the results of individual content uniformity evaluation was calculated in accordance with the uniformity of dosage unit section in Korean Pharmacopoeia.

Acceptance value=$|M-\bar{X}|+ks$

M=reference value, X=mean of individual contents
k=acceptability constant (2.4 when n=10), s=standard deviation <Analytical Conditions for Salmeterol and Fluticasone>
Column: stainless column (internal diameter of about 4.6 mm and length of 15 cm) packed with octadecylsilyl silica gel (diameter of 5 μm).
Mobile phase: methanol:acetonitrile:water=50:16:34 (v/v/v) containing 0.6% (w/v) of ammonium acetate
Detector: UV-absorption detector (absorbance at 228 nm)
Column temperature: 40° C.
Flow rate: 1.0 mL/min
Injection volume: 100 μL <Analytical Conditions for Tiotropium>

Column: stainless column (internal diameter of about 4.6 mm and length of 15 cm) packed with octadecylsilyl silica gel (diameter of 5 μm).

Mobile phase: a mixed solution prepared by adding 300 mL of acetonitrile with 700 mL of a solution prepared by adding 1.79 g of sodium heptanesulfonate monohydrate in 1 L of water whose pH value was adjusted to 3.2 using a phosphoric acid Detector: UV-absorption detector (absorbance at 240 nm)
Column temperature: 30° C.
Flow rate: 2.0 mL/min
Injection volume: 10 μL

TABLE 10

Content uniformity (%) of active ingredients in the dry powder inhalation formulation of Example 1

|  | Salmeterol (%) | Fluticasone (%) | Tiotropium (%) |
| --- | --- | --- | --- |
| 1 | 96.2 | 102.6 | 96.2 |
| 2 | 94.6 | 96.7 | 96.8 |
| 3 | 94.9 | 103.7 | 99.3 |
| 4 | 103.2 | 94.6 | 101.0 |
| 5 | 96.8 | 92.6 | 99.0 |
| 6 | 104.6 | 98.5 | 101.7 |
| 7 | 99.0 | 103.1 | 99.0 |
| 8 | 106.2 | 96.6 | 97.4 |
| 9 | 102.6 | 103.6 | 99.9 |
| 10 | 102.5 | 103.9 | 100.9 |
| Mean | 100.1 | 99.6 | 99.1 |
| S.D. | 4.3 | 4.3 | 1.9 |
| Acceptance Value | 10.2 | 10.3 | 4.4 |

TABLE 11

Content uniformity (%) of active ingredients in the dry powder inhalation formulation of Example 2

|  | Salmeterol (%) | Fluticasone (%) | Tiotropium (%) |
| --- | --- | --- | --- |
| 1 | 96.4 | 100.2 | 99.4 |
| 2 | 98.7 | 100.5 | 99.1 |
| 3 | 98.6 | 100.7 | 101.3 |
| 4 | 96.4 | 99.6 | 101.5 |
| 5 | 100.8 | 96.9 | 96.1 |
| 6 | 98.6 | 100.6 | 100.6 |
| 7 | 100.8 | 100.0 | 98.4 |
| 8 | 100.8 | 100.7 | 101.5 |
| 9 | 100.9 | 100.6 | 101.4 |
| 10 | 96.5 | 98.5 | 92.9 |
| Mean | 98.9 | 99.8 | 99.2 |
| S.D. | 1.9 | 1.2 | 2.8 |
| Acceptance Value | 4.6 | 3.0 | 6.8 |

TABLE 12

Content uniformity (%) of active ingredients in the dry powder inhalation formulation of Comparative Example 1

|  | Salmeterol (%) | Fluticasone (%) | Tiotropium (%) |
| --- | --- | --- | --- |
| 1 | 92.3 | 88.6 | 101.6 |
| 2 | 88.5 | 110.7 | 112.2 |
| 3 | 120.6 | 112.6 | 88.7 |
| 4 | 95.6 | 98.7 | 89.4 |
| 5 | 98.6 | 87.6 | 105.7 |
| 6 | 92.4 | 92.4 | 110.7 |
| 7 | 85.6 | 120.4 | 92.7 |
| 8 | 110.8 | 88.7 | 86.9 |
| 9 | 106.7 | 92.4 | 93.4 |
| 10 | 98.6 | 98.6 | 105.5 |
| Mean | 99.0 | 99.1 | 98.7 |
| S.D. | 10.8 | 11.6 | 9.5 |
| Acceptance Value | 26.0 | 27.8 | 22.9 |

As shown in Tables 10 to 12 above, acceptance values of the three active ingredients in the dry powder inhalation formulations of Examples 1 and 2 were less than 15, ensuring the uniformity of the formulations. However, the acceptance values of the active ingredients in the dry powder inhalation formulation of Comparative Example 1 exceeded 20, and thus, showed inconsistency in the content uniformity.

TEST EXAMPLE 2

Aerodynamic Size Distribution of Active Ingredients

Figure 1:
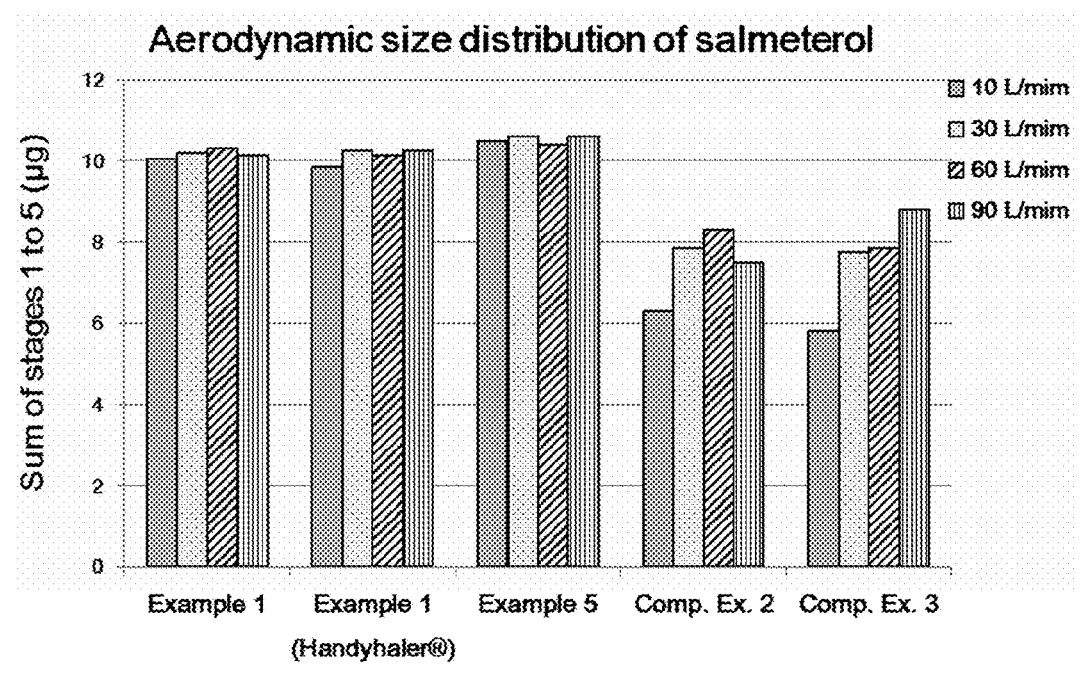

The aerodynamic size distribution of the dry powder inhalation formulation prepared in Examples 1 and 5, and Comparative Examples 2 and 3 were tested using an inhalation device (AEROLIZER®) with Apparatus 3 (Anderson Cascade Impactor), and the contents of the pharmaceutically active ingredients were measured from stages 1 to 5. The formulation of Example 1 was subjected to an additional test using a different inhalation device (HANDIHALER®). The samples were analyzed using the analysis method used in Test Example 1 with four different flow rates, 10 L/min, 30 L/min, 60 L/min and 90 L/min. Also, relative humidity of the testing environment was kept in a range of 45 to 60% to minimize the effect of static electricity on the mixture particles during the inhalation. The results are shown in FIGS. 1 to 3.

Figure 2:
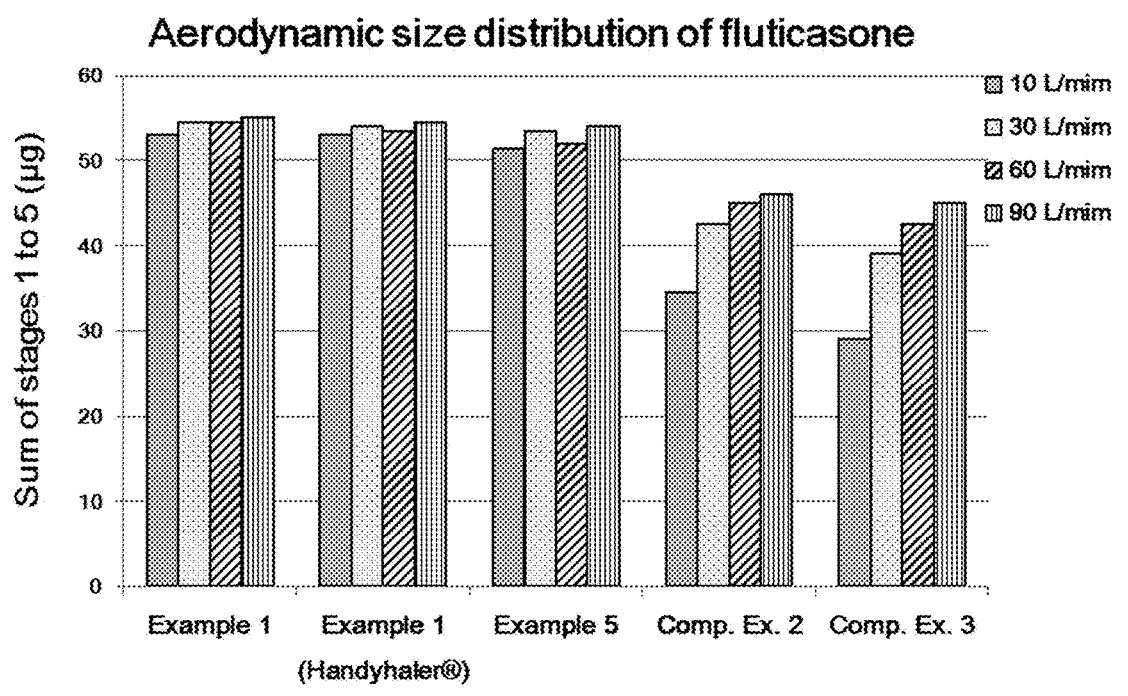
Figure 3:
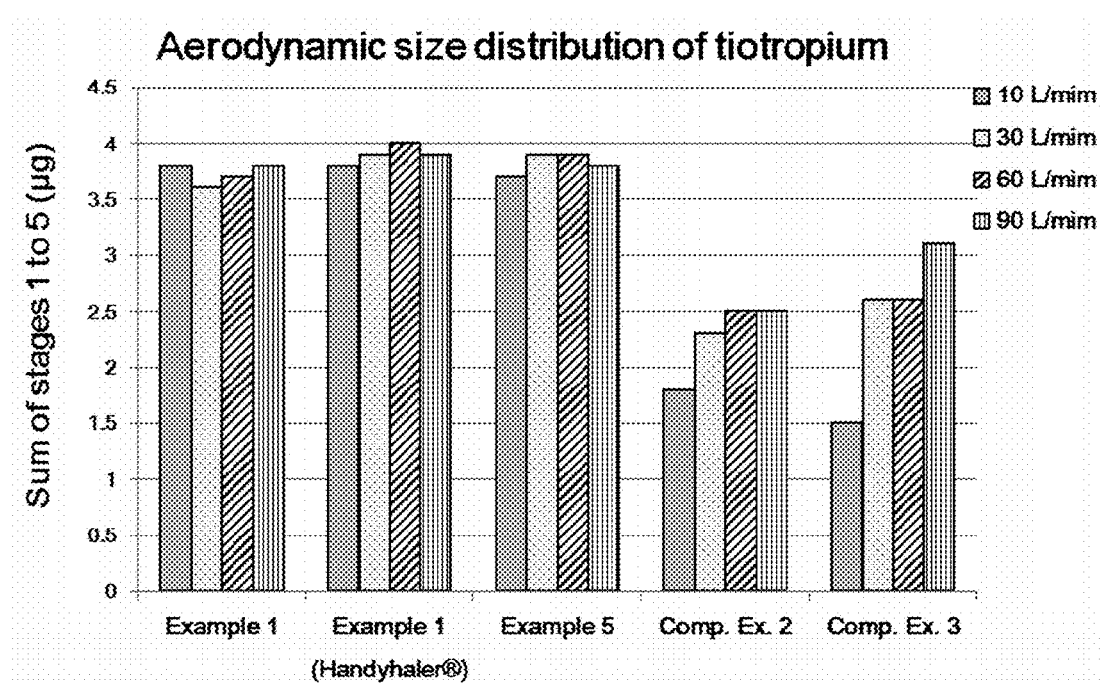

As shown in FIGS. 1 to 3, the results of the contents during stages 1 to 5, which indicate the effective dose of the dry powder inhalation formulation of Examples 1 and 5 were relatively consistent at the range of 10 L/min to 90 L/min of the flow rate, and no fluctuation of particle size distribution in accordance with the flow rate changes was observed. On the contrary, the amount of the individual contents of Comparative Examples 2 and 3 was less than that of Examples 1 and 5, and a high fluctuation in the particle size distribution in accordance with the flow rate changes was observed as well. In the case of Comparative Example 2, the amount of lactose was too small, and the size of the carrier as well as the method for mixing were inappropriate so that a large amount of the active ingredients remained in the capsule after the inhalation of the formulation, and also the high fluctuation in the particle size distribution in accordance with the flow rate changes was observed. Also, in the case of Comparative Example 3, it seems that a considerable change in the particle size distribution was caused owing to inappropriate particle size of the compositions.

What is claimed is:

1. A method for preparing a dry powder for inhalation formulation comprising salmeterol xinafoate, fluticasone propionate, and tiotropium bromide as active ingredients, and a carrier, which method comprises the steps of:

(1) applying 5 to 20 wt % of the carrier, based on the total amount of the carrier, onto inner wall of a mixer;
(2) triturating the active ingredients with 5 to 20 wt % of the carrier, based on the total amount of the carrier, to obtain triturated active ingredients; and
(3) placing the triturated active ingredients of step (2) and the remaining carrier in the mixer prepared in step (1), and conducting mixing and pulverizing the triturated active ingredients and the remaining carrier by applying a force not to substantially alter the size of the particles, to give the dry powder comprising pulverized active ingredients and pulverized carrier,
wherein the dry powder has an average particle size in a range of 30 to 120 μm.

2. The method for preparing the dry powder for inhalation formulation of claim 1, wherein the average size particle of said pulverized active ingredients is greater than 0.1 μm and less than or equal to 10 μm, and the average size particle of the pulverized carrier is in a range of 30 to 120 μm.

3. The method of claim 1, wherein the dry powder has an average particle size in a range of 55 to 65 μm.

4. The method of claim 1, wherein the carrier is selected from the group consisting of a monosaccharide, disaccharide, polysaccharide, polyalcohol, and a hydrate thereof.

5. The method of claim 4, wherein the carrier is lactose monohydrate.

* * * * *